United States Patent [19]

Scuitto et al.

[11] Patent Number: 4,976,541
[45] Date of Patent: Dec. 11, 1990

[54] AUTOMATIC ATOMIC-ABSORPTION SPECTROMETRY METHOD

[75] Inventors: Theodore J. Scuitto, Grants Pass; Thomas J. Scuitto, Talent; Al E. Bernhard, Brooking, all of Oreg.

[73] Assignee: Analyte Corporation, Medford, Oreg.

[21] Appl. No.: 298,779

[22] Filed: Jan. 17, 1989

Related U.S. Application Data

[63] Continuation of Ser. No. 14,873, Feb. 17, 1987, abandoned.

[51] Int. Cl.$^5$ .................................................. G01J 3/42
[52] U.S. Cl. .................................. 356/300; 356/311; 356/328
[58] Field of Search ............... 356/311, 312, 315, 316, 356/319, 323, 325, 326, 328, 300

[56] References Cited

U.S. PATENT DOCUMENTS

| | | | |
|---|---|---|---|
| 3,523,748 | 8/1970 | Chrisholm et al. | 356/315 |
| 3,655,288 | 4/1972 | Lieberman et al. | 356/315 |
| 4,300,833 | 11/1981 | Harnly et al. | 356/312 |

OTHER PUBLICATIONS

Hewlett–Packard, *Analytical Advances*, Autumn 1968, vol. 1, No. 1, pp. 1–16.
Hewlett–Packard, Bulletin 5960–Model 5960A Atomic Absorption Photometer.
Ediger, *American Laboratory*, Feb. 1978, pp. 67, 68, 75 and 76.
"Instrumentation '78", C & EN, Mar. 13, 1968, pp. 32–36, 40, 42–45, 47, 48, 54, 56, 59.
Dagnall et al, *Talanta*, vol. 13, Jun. 1966, pp. 803–808.
Demers, Applied Spectroscopy, vol. 22, No. 6, Nov.–Dec. 1968, pp. 797–798.
Norelco–UNICAM brochure, pp. 1–8.

*Primary Examiner*—F. L. Evans
*Attorney, Agent, or Firm*—Ashen Martin Seldon Lippman & Scillieri

[57] ABSTRACT

Each sample is analyzed for all desired elements before starting the next sample, using thermal or nonthermal atomizing devices fro liquid or solid samples. Other new features include the grating drive, lamp-carousel alignment, pulsed atom source, lamp-drift compensation, and dynamic range control. The grating is driven by an arm, the arm by a taut band wound on a drum, and the drum directly by a motor. The lamp carousel mounts on an "L"-shaped rocker with one horizontal and one vertical arm. The carousel rotates on a horizontal axis at the end of the vertical arm. The rocker itself pivots on a horizontal axis at the corner of the L; it is driven about its axis by a motor and screw at the other end of the L. Carousel rotation on its axis moves the right lamp into position and adjusts it accurately in a vertical direction. Pivoting of the rocker simultaneously on its corner axis positions the lamp accurately in a horizontal direction. The pulsed atom source is a combined angled-gas-jet-and-discharge unit. During pulses it yields high absorption with better detectability limits; average power is lower. The lamp-drift compensator makes double duty of the absorber pulsation to obtain a lamp-intensity reading between pulses. Dynamic range control is obtained by even further exploiting the pulsation, namely by taking measurements at a known delay (and decay) time after each pulse.

11 Claims, 1 Drawing Sheet

AUTOMATIC ATOMIC-ABSORPTION SPECTROMETRY METHOD

This is a continuation of co-pending application Ser. No. 07/014,873 filed on Feb. 17, 1987, now abandoned.

BACKGROUND

1. Field of the Invention

This invention relates generally to atomic-absorption spectrometry; and more particularly to a new spectrometer for obtaining multiple atomic-absorption measurements much more quickly, easily and accurately.

2. Prior Art

A commonly used instrumental analysis method for the elemental analysis of various materials for trace and minor elements is the atomic absorption method. In the most used manifestation the analytical instrument consists of a means for generating a vapor such as a nebulizer; a burner assembly to disassociate into free atoms the vapor delivered by the nebulizer: a source of monochromatic light such as a hollow cathode lamp which light is directed through the atomized vapor, and a device for isolating and measuring the monochromatic light after it has passed through the atomized vapor. The quantitative measurement of the elements present in the vapor and thus the liquid sample from which the vapor was derived is made by comparing the intensity of the monochromatic light characteristic of an element after absorption in the burner flame to the unabsorbed intensity of the light source.

The wavelength-region isolating device, called a monochromator, requires some mechanism for driving a diffraction grating (or other dispersive element). Some prior artisans have driven gratings with sine-bar devices, or direct motor-shaft-to-grating connections. Others have used nonlinear drums or cams for interconnecting grating arms with motors.

The sine-bar mechanism produces a drive whose angular rotation of the motor is substantially directly proportional to the wavelength passing through the monochromator. This drive requires a worm gear that is highly accurate throughout its length, and it requires a point of contact between the carriage that rides on the worm gear and the arm that slides along the arm. The worm gear and the sliding contact are both subject to wear.

Direct grating mount to a motor shaft does not introduce the wearing surfaces of the sine bar, and it allows rapid scanning of the wavelength. Connecting the motor shaft directly to the grating shaft produces only one mathematical relationship between the motor position and the wavelength passing through the monochromator: the relationship is nonlinear in wavelength and the inverse of wavelength (frequency or photon energy). A special high precision motor is required to achieve the necessary wavelength precision and accuracy, and the motor must be driven in such a manner that the nonlinearity is compensated for when wavelength scanning is recorded on a strip chart recorder for example.

Next we consider the nonlinear drum or cam (mounted on a motor shaft) that is in direct contact with the grating arm. In this case the wavelength range covered is limited by the extent of the motion of the arm as the cam rotates through one full revolution. A compromise is necessary between the range of the wavelength region covered and the accuracy and precision with which the wavelength can be set.

We shall only very briefly discuss prior-art devices for lamp positioning and alignment. They are generally rudimentary and unsatisfactory. Most of these devices have a lamp-carrying carousel. For accurate alignment each individual lamp must be manually adjusted on its mount.

Prior AA spectrometers are also limited by difficulty in obtaining optical absorption measurements in a favorable range. Precision and accuracy depend greatly on the range in which measurements are made.

It should be mentioned that some prior workers have used pulsed lamps. Pulsing of lamps allows signal handling on an a. c. basis, with various well-known advantages.

In atomic-absorption work it is necessary to collect some information as to the intensity of the light-source signal both in the presence of and in the absence of an absorber. This is usually done by atomizing distilled water, which is essentially nonabsorbing for the monochromatic light used to measure the element, and recording the signal; and then ceasing the introduction of distilled water into the flame and instead atomizing the liquid sample to be analyzed, and recording the signal. This is done rather frequently to compensate for changes in the light source intensity with time.

We will further mention that heretofore an important limitation of absorption methods is the limited dynamic range (of absorbance values and therefore concentrations) over which accurate measurements can be made.

SUMMARY OF THE DISCLOSURE

The spectrometer system consists of the following basic parts:

1. A light source that has up to 16 different hollow cathode lamps mounted in a carousel so that each lamp can be rapidly and accurately positioned into the optical path when it is needed.

2. A sampling system that converts a sample into an atomic vapor so that the absorption of the atoms can be determined and related to the concentration in the original sample.

3. A monochromator that isolates the wavelength region of interest, converts the light into an electronic signal via a photomultiplier tube and displays and records the results.

4. A computer system that controls the system and processes and displays the measurements.

Our instrument differs in two fundamental ways from currently existing multielement AA instruments. First, it analyzes each sample completely for all the desired elements, before moving on to the next sample. Conventional multielement AA's analyze a group of, say, 50 samples by determining a single element in all of them, then going to a second element, and so on. Second, our instrument is intended for use with the Analyte Atomsource ™ non-thermal Atomizer, which is designed for the analysis of solid, undissolved samples. Conventional AA's use either a flame or a furnace atomizer, both of which are most suitable for the analysis of liquids.

Equipped with the Atomsource Atomizer, our spectrometer preserves the flame AA advantages of specificity and ease of use, but provides even better precision (0.1% RSD), and the ability to determine a wide range of concentrations, from ppm to constituent levels, with little or no sample preparation. Our invention also has good sensitivity for refractory elements such as B, Si, Ti, and W, which give problems by conventional AA. A laboratory might therefore consider the use of the present AA instrument instead of, or as a supplement to, an X-ray fluorescence or an arc/spark emission spectrometer.

The present invention is equipped with a turret that can hold sixteen hollow-cathode lamps, some of which can be multielement sources. If the first element to be determined in a given sample is, say, silver, and the second is iron, the automated operation is as follows:

The source optics of the instrument set themselves to accept the light from the silver hollow cathode lamp, while the monochromator drives to the preselected silver wavelength. Immediately after the silver has been determined, the optics move to select the emission from the iron lamp, while the monochromator moves to the iron wavelength, and so on until the sample has been completely analyzed. The time for each determination can be as low as 5 seconds per element. A sample can be analyzed for ten elements in 60 seconds, and for 20 elements in under two minutes.

Physically, our invention consists of three modules. The optical module includes the lamp turret, monochromator, power supplies, and microprocessor controllers. The second module is the Atomsource Atomizer. The third module is an IBM-compatible personal computer, which provides all the required control and intelligence for instrument and atomizer.

The present instrument can also be provided with a conventional atomic absorption flame atomizer. In the flame mode, our invention has performance that is approximately equivalent to that of a good sequential ICP (inductively coupled plasma) spectrometer. Our invention has, however, far fewer spectral interferences, and can use all the well-established atomic absorption methods that have been developed over the past 25 years. Our invention is therefore worth considering as an alternative to sequential ICP instruments.

Our new spectrometer incorporates these improvements:
1. Grating drive
2. Lamp carousel optical alignment method
3. Pulsed atom source
4. Compensation method for lamp intensity drift
5. Dynamic range control These will be discussed in order.

The grating is driven by an arm, the arm in turn by a taut band wound on a drum, and the drum directly by a motor. The arm is spring-biased to hold the band taut.

This drive system is far less susceptible to frictional wear than prior-art sine-drive systems. It is also far less demanding of motor-drive precision than earlier direct-motor-drive systems.

The lamp-carousel subsystem includes an "L"-shaped rocker carriage, with one horizontal and one vertical arm. The carousel is mounted to rotate on a horizontal axis at the end of the vertical arm. The rocker itself pivots on a horizontal axis at the corner of the L; it is driven about its axis by a motor and near-vertical screw at the other end of the L.

Rotation of the carousel on its axis moves the right lamp into position and adjusts it accurately in the vertical direction. Pivoting of the rocker simultaneously about its corner axis positions the lamp accurately in the horizontal direction.

The pulsed atom source is a combined angled-gas-jet-and-discharge device. During the pulses it provides high absorption with better detectability limits; average power is lower.

Prior art includes pulsing a hollow cathode lamp, which is a glow discharge. It is not obvious however from this prior art that this special combined discharge can be pulsed. For example, it would be reasonable to expect that a gas jet when suddenly turned on would blow out the electrical discharge. It would also be reasonable to expect that the presence of a jet prior to turning on the electrical discharge would make it impossible to rapidly establish during the electrical pulse an electrical discharge in the rapidly moving jet. Even if it were not possible to establish a pulsed mode of operation (where the jet or electrical discharge are suddenly turned on) it is still possible to establish the previously known continuous mode of operation of the combined discharge by the different means of slowly turning on the jet.

The lamp-drift compensator makes double duty of the absorber pulsation to obtain a lamp-intensity reading between pulses. This intensity reading can be used to provide correction, i.e., establish a more stable baseline, in view of lamp-intensity fluctuations.

Dynamic range control is obtained by even further exploiting the pulsation, namely by taking measurements at a known delay (and decay) time after each pulse. Decay of the discharge is reproducible; hence the time delay used can be translated into an absorption-value correction factor.

All of the foregoing operational principles and advantages of the present invention will be more fully appreciated upon consideration of the following detailed description, with reference to the appended drawings, of which:

DETAILED DESCRIPTION OF THE PREFERRED EMBODIMENTS

1. Grating Drive.

The monochromator has a grating that disperses light of different wavelengths in different directions. The wavelength of light that passes through the monochromator is determined by the rotational position of the grating. The rotational position of the grating is determined by a unique drive mechanism.

Figure 1:
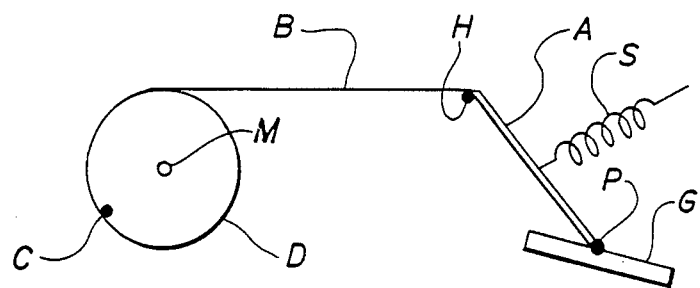
FIG. 1 is a simplified and highly schematic diagram of the taut-band grating drive, which in principle may be either in elevation or in plan.

FIG. 1 is a schematic diagram of the grating and its unique drive mechanism. The grating is mounted so that its front surface G pivots about an axis at point P. An arm A is attached to the grating mount to allow the grating to be rotated as the taut band or wire B pulls on the arm. The taut band or wire is connected to the arm at a hinge point H. A spring S helps to keep the band or wire taut. The band is connected to a drum D at point C and wraps around drum, less than one time or up to many times around the drum. The drum is rotated about its axis M by a motor (stepping, synchronous, or servo).

This mechanism is unique for at least two reasons:

(1) because a taut band or wire connects the arm of the grating drive to a motorized drum and (2) because the particular arrangement of the parts causes the angular position of the grating, and more importantly the wavelength that passes through the monochromator, to be related by a unique mathematical function to the angle of drum D; no other grating drive mechanism relates the angle of a motor shaft to the angle of the grating drive by this same mathematical function. This mathematical function depends upon the length of the arm A, the length of the taut member B, the diameter of the drum D, the distance between the pivot points of the drum M and the grating P, and the shape of the drum. The drum may be circular in shape, or it may be machined to have a shape that produces a particular desirable mathematical relationship. For example, the drum could be shaped so that the angle of the drum position could be directly proportional to the energy of the light passing through the monochromator (that is, inversely proportional to the wavelength). Or the drum could be shaped so that the angle of the drum position is directly proportion to wavelength.

When the functional relationship between motor position and wavelength deviates from a desired relationship, the deviation can be corrected by the computer supplying an offset number for the position of the motor. In this case the offset number can be calculated more quickly when the deviation has the simplest mathematical form. The versatility of the taut band system to adjust the functional relationship by selecting dimensions listed in the previous paragraph helps to achieve a deviation with the simplest mathematical form.

As will be recalled, we have explained above various disadvantages of sine-bar drives, direct motor-to-grating drives, and nonlinear cam or drum systems. We there noted that prior-art drive systems of the sine-bar type are particularly susceptible to wear.

The taut band system is not subject to such wear because there are no gears if the motor is connected directly to the drum shaft M, and there is no sliding contact that moves along the arm A. The taut band system also allows the wavelength to be changed much more rapidly than would be reasonable (because of rapid wear) for the worm gear system. (The worm gear in this application must have a very fine pitch because the grating must be positioned with great accuracy to achieve a reproducible wavelength setting that is better than 0.1 nanometers. The fine pitch requires exceptionally high speed rotation for rapid scanning.)

In addition to being more versatile than the direct drive motor system in the functional relationship between motor shaft position and wavelength, the taut band system does not require a motor with such high precision when the diameter of the drum D is considerably less than the length of the arm A. The demand on precision is decreased by approximately the ratio of these two dimensions.

The taut band system is able to cover a wide wavelength range with accuracy, especially when a circular drum is used and the diameter of the drum is smaller than the length of the arm. (In this case the taut band wraps around the drum more than once during a wide wavelength scan.) Unlike the cam drive, when a nonlinear drum is used with the taut band system, the functional relationship between motor position and wavelength is determined not only by the shape of the drum, but as mentioned above also by the length of the arm A, the length of the taut member B, the average diameter of the drum D, and the distance between the pivot points of the drum M and the grating P. The taut band system has no member that rubs against the grating arm as does the cam system.

Another advantage is that this is more efficient than the acme lead screws and therefore energy required and drive costs are lower for the same performance.

2. Lamp carousel optical alignment

Each different chemical element whose absorption is to be determined requires a different hollow cathode lamp. In a few cases one lamp may suffice for a few different elements. Up to 16 lamps are mounted on a lamp carousel that rapidly rotates each lamp into an accurately determined position in the optical path when the lamp is needed.

Figure 2:
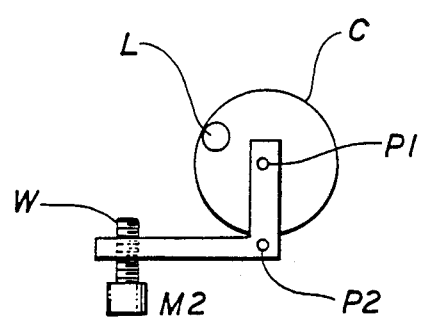
FIG. 2 is a like diagram of the lamp-carousel positioning system, except that it is preferably considered as an elevational view.

A unique (and necessary) feature of the carousel is its ability to accurately and rapidly position each lamp that is present in the carousel. It does this rapidly because of the way that the carousel is pivoted about two points P1 and P2 in FIG. 2. Pivoting about P1 moves the proper lamp into position and positions it accurately in a substantially vertical direction. Pivoting about P2, which occurs essentially during the same time that the movement about P1 occurs, positions the lamp accurately in a substantially horizontal direction. FIG. 2 shows the motion about P2 being done with a worm gear W driven by a motor M2. Other driving methods are possible, such as a direct connection of the shaft of P2 to a motor shaft.

A unique feature of the carousel is the use of pivoting around two pivots to align the lamp in the horizontal and vertical directions. Pivoting can be done more rapidly and with a simpler mechanism than moving the entire carousel horizontally along a linear translation stage for example.

In operation, when a lamp is first mounted in the carousel, the computer system that controls the spectrometer scans the lamp alternately about P1 and P2 two or three times in each direction to determine when the lamp is centered on the optical axis. The two motor positions (for the motors that drive the carousel about P1 and P2) are then stored in memory for later use to position the lamp when the lamp is needed during a chemical analysis.

3. Pulsed atom source

One claim here is for a pulsed means of removing atoms from the surface of a solid sample (and keeping the atoms in a substantially free state long enough for them to be observed) that combines the removal effects of (a) at least one jet of gas disposed adjacent such sample surface and pointing at a substantially nonzero angle toward such surface and (b) a low pressure electrical discharge. There are three ways to pulse this special type of discharge (1) pulse the electrical discharge, (2) pulse the gas jet, and (3) pulse both simultaneously.

Another claim is that pulsing the atom source has the advantage of getting high absorption generated by high current pulses without the instability associated with high current DC operation. This also permits better limits of detectability for less power costs.

4. Compensation method for lamp intensity drift

It is uniquely possible when using a pulsed atom source to supply the absorbing atoms from the sample material, to obtain these two signals by recording the signal before each pulse and then recording the signal after the pulsed atom source has been turned on and the absorbing sample atoms are in the optical path. The general claim here is either (a) this method of obtaining these two signal before and during each pulse or/and (b) the use of a pulsed absorber to allow this method to be used without using an external force to physically manipulate the nonabsorber and absorber between these measurements.

By making these two measurements for each pulse, it is possible to compensate for relatively rapid changes with time in the light source intensity. If the measurement of the nonabsorber signal is made just prior to (within micorseconds of) turning on the sampling pulse, then the compensation can be achieved on a time scale that is considerably shorter than can be done with the methods that involve physical manipulation (even with mechanically vibrating systems); more rapid changes in the lamp intensity can thereby be tolerated.

This pulsed method also has the advantage of observing the same part of the beam from the lamp for both signals, and with the same optical components in the beam. Double beam systems either observe different parts of the beam at the same time, or the same part of the beam with different optical components in each beam. When different parts of the beam are observed, each part may behave somewhat differently, and the compensation will not, then, be completely accurate. When the same part is observed by different optical components, then the optical components may not be identical, causing the compensation to be somewhat inaccurate.

The claims presented here are not restricted to solid sample atomization but apply to flame atomization as well.

Another embodiment of this claim is the use of a pulsed light source that is synchronized with the pulsed absorbing source so that a nonabsorber light measurement pulse occurs just prior to the pulse of the absorbing source, and another occurs after the absorbing source is pulsed on.

Also the separation of the atomization process from the absorption measurement temporally, also eliminates the emission noise from the absorption measurement thus improving detection limits.

In addition high intensity light source pulses reduce front end noise improving detection limits.

5. Dynamic range control.

The use of a pulsed source of absorbing atoms allows the dynamic range to be easily extended without changing wavelength and without a significant loss of time or sample. This unique method involves making measurements at a known delay time after the absorber pulse is turned off (and the absorption has had a chance to decay) when the absorption is too high during the pulse.

When a continuous light source is used, then many measurements can be made at fixed delay-time intervals after each pulse. The data for the best delay-time interval are then selected for use after the measurements have been completed. When a pulsed light source is used, then a measurement made during a previous absorber pulse can be used to select the delay time to pulse the lamp for the present absorber pulse. Alternatively, the delay time can be set before a sample is run if some previous knowledge of the approximate range of concentration is available for the sample.

In practice, the relationship between delay time and absorbance relative to the absorbance that occurs during the absorber pulse is determined by measurement. This relationship is used to establish a large dynamic range over which concentrations can be accurately compared; that is, the delay time and the measured absorbance are both entered into this relationship to obtain an effective absorbance (or parameter with some other name) for comparison purposes over a large dynamic range of concentrations.

It will be understood that the foregoing disclosure is intended to be merely exemplary, and not to limit the scope of the invention—which is to be determined by reference to the appended claims.

We claim:

1. A method for making atomic-absorption measurements for a plurality of samples, comprising the steps of:
    selecting a particular sample; and
    then analyzing the selected sample for a plurality of elements in turn, one at a time in a preestablished sequence, by making at least one atomic-absorption measurement corresponding to each element of the plurality, before making any atomic-absorption measurement for any other sample; and
    then repeating the selecting and analyzing steps for a plurality of different particular samples;
    wherein the analyzing step comprises, for one particular element of the plurality, the substeps of:
    positioning the selected sample for measurement;
    automatically selecting and moving into measurement position a particular lamp that emits a narrow spectral line of a particular wavelength used for analyzing the selected sample for the particular element;
    automatically adjusting a monochromator to that particular wavelength of that spectral line; and
    then automatically sensing the amount of light of that particular wavelength received from that particular lamp through the monochromator and through the selected sample, for use in determining the amount of the particular element in the selected sample.

2. The method of claim 1, wherein the analyzing step further comprises, for a second particular element of the plurality, the subsequent substeps of:
    while the selected sample remains positioned for measurement, automatically selecting and moving into measurement position a second narrow-line lamp that emits a spectral line of a second wavelength used for analyzing the selected sample for the second particular element;
    while the selected sample remains positioned for measurement, automatically adjusting a monochromator to the second wavelength; and
    then, while the selected sample remains positioned for measurement, automatically sensing the amount of light of the second wavelength received from the second lamp through the monochromator, for use in determining the amount of the second particular element in the selected sample.

3. The method of claim 1, wherein the analyzing step further comprises, for a particular element of the plurality, the subsequent substeps of:
    while the selected sample and the particular lamp remain in position, automatically adjusting the monochromator to a second particular wavelength used for analyzing the selected sample, said second particular wavelength corresponding to a second narrow spectral line emitted by that same lamp; and
    then, while the selected sample remains positioned for measurement, automatically sensing the amount of light of that second wavelenght received from that same lamp through the monochromator, for use in determining the amount of the particular element in the same selected sample.

4. A method for making atomic-absorption measurements for at least one sample, with respect to a plurality of elements; said method comprising the steps of:
   automatically determining optimum instrument settings for each element, including the position of a lamp used for making a measurement for that element; and
   automatically recording values representative of the determined optimum instrument settings for each element;
   after the determining and recording steps, selecting a particular sample; and
   then automatically analyzing the selected sample for a plurality of elements in turn, one at a time in a preestablished automatic sequence, by making at least one atomic-absorption measurement corresponding to each element of the plurality; and wherein:
   the analyzing step comprises, for each element, the substep of automatically recalling the recorded values for that element;
   the analyzing step also comprises, for each element, the substep of automatically using the recalled values to restore the determined optimum instrument settings for that element;
   the determining step comprises scanning each lamp along substantially orthogonal directions to determine an optimum position of that lamp relative to an optical axis;
   the values recorded in the recording step comprise lamp-position values representative of the optimum position of each lamp along the substantially orthogonal directions;
   the recalling substep, for each element, comprises recalling the recorded lamp-position values for a lamp associated with that element; and
   the using substep, for each element, comprises using the recalled lamp-position values to control a servomechanism in automatic repositioning of the associated lamp at the optimum position along the substantially orthogonal directions.

5. The method of claim 4, wherein:
   said scanning comprises scanning each lamp at least twice alternately along said substantially orthogonal directions.

6. The method of claim 4, wherein:
   in the analyzing step, said at least one atomic-absorption measurement corresponding to each element of the plurality is made before making any atomic-absorption measurement for any other sample.

7. The method of claim 6, wherein:
   the plurality of elements constitutes all of the elements of interest for the selected sample.

8. The method of claim 4, further comprising the step of:
   after the selecting and analyzing steps, repeating the selecting and analyzing steps for a plurality of different particular samples.

9. A method for making atomic-absorption measurements for a plurality of samples, comprising the steps of:
   selecting a particular sample; and
   then analyzing the selected sample for a plurality of elements in turn, one at a time in a preestablished sequence, by making at least one atomic-absorption measurement corresponding to each element of the plurality, before making any atomic-absorption measurement for any other sample; and
   then repeating the selecting and analyzing steps for a plurality of different particular samples;
   wherein the analyzing step comprises, for one particular element of the plurality, the substeps of:
   positioning the selected sample for measurement;
   having in, or moving into, measurement position a lamp that emits light used for analyzing the selected sample for the particular element;
   automatically isolating, from the light emitted by the lamp, a narrow spectral band about a particular wavelength used for analyzing the selected sample for the particular element, by automatically adjusting a monochromator to that particular wavelength of that spectral band; and
   then automatically sensing the amount of light of that particular wavelength received in that isolated band through the monochromator and through the selected sample, for use in determining the amount of the particular element in the selected sample.

10. The method of claim 9, wherein the analyzing step further comprises, for a second particular element of the plurality, the subsequent substeps of:
   while the selected sample remains positioned for measurement, automatically isolating a second narrow spectral band, about a second wavelength, used for analyzing the selected sample for the second particular element;
   while the selected sample remains positioned for measurement, automatically adjusting a monochromator to the second wavelength; and
   then, while the selected sample remains positioned for measurement, automatically sensing the amount of light of the second wavelength received in the second band through the monochromator and through the selected sample, for use in determining the amount of the second particular element in the selected sample.

11. A method for making atomic-absorption measurements for a plurality of samples, comprising the steps of:
   selecting a particular sample; and
   then analyzing the selected sample for a plurality of elements in turn, one at a time in a preestablished sequence, by making at least one atomic-absorption measurement corresponding to each element of the plurality, before making any atomic-absorption measurement for any other sample; and
   then repeating the selecting and analyzing steps for a plurality of different particular samples;
   wherein the analyzing step comprises, for one particular element of the plurality, the substeps of:
   positioning the selected sample for measurement;
   having in, or moving into, measurement position a lamp that emits light used for analyzing the selected sample for the particular element;
   automatically isolating, from the light emitted by the lamp, a narrow spectral band about a particular wavelength used for analyzing the selected sample for the particular element; by automatically adjusting a monochromator to that particular wavelength of that spectral band;
   then automatically sensing the amount of light in that particular band received through the monochromator and through the selected sample, for use in determining the amount of the particular element in the selected sample;
   then, while the selected sample and the lamp remain in position, automatically selecting, from the light emitted by the lamp, a second narrow spectral band about a second particular wavelength used for analyzing the selected sample for the particular element;

then, while the selected sample and the lamp remain in position, automatically adjusting the monochromator to the second particular wavelength used for analyzing the same selected sample; and then, while the selected sample remains positioned for measurement, automatically sensing the amount of light in the second band received from the same lamp through the monochromator and through the selected sample, for use in determining the amount of the particular element in the same selected sample.

* * * * *